US006537576B1

(12) United States Patent
Lindahl et al.

(10) Patent No.: US 6,537,576 B1
(45) Date of Patent: Mar. 25, 2003

(54) BIOLOGICALLY ACTIVE COMPOSITION

(75) Inventors: Åke Lindahl, Skurup (SE); Håkan Hagslätt, Bjärred (SE); Catharina Benediktsson, Malmö (SE); Richard Bryland, Malmö (SE)

(73) Assignee: Bioglan AB, Malmö (SE)

( * ) Notice: Subject to any disclaimer, the term of this patent is extended or adjusted under 35 U.S.C. 154(b) by 0 days.

(21) Appl. No.: 09/700,176

(22) PCT Filed: May 12, 1999

(86) PCT No.: PCT/SE99/00823

§ 371 (c)(1),
(2), (4) Date: Jan. 29, 2001

(87) PCT Pub. No.: WO99/58108

PCT Pub. Date: Nov. 18, 1999

(30) Foreign Application Priority Data

May 14, 1998 (SE) ................................. 9801704

(51) Int. Cl.[7] .............................. A61K 9/14; A61K 31/74; A61K 31/56; A01M 25/34; A01M 25/00
(52) U.S. Cl. ..................... 424/486; 424/78.31; 424/411; 514/179; 514/937
(58) Field of Search .............................. 424/486, 78.31, 424/411; 514/179, 937

(56) References Cited

U.S. PATENT DOCUMENTS 4,940,701 A  7/1990  Davis ...................... 514/179

FOREIGN PATENT DOCUMENTS

| DD | 217 989 | 1/1985 |
| DE | 44 00 770 | 2/1995 |
| EP | 0 430 491 | 6/1991 |
| GB | 2306885 A | 5/1997 |
| WO | WO 97/00670 | * 1/1997 |
| WO | WO97/10812 | 3/1997 |

OTHER PUBLICATIONS

M.F. Coldman et al., *Enhancement of Percutaneous Absorption by the Use of Volatile: Nonvolatile Systems in Vehicles*, J. Pharm. Sci., 58, No. 9, 1969, pp. 1098–1102.

Rainer Lichtenberger et al., *Polymer Films From Aqueous Latex Dispersing as Carriers for Transdermal Delivery of Lipophilic Drugs*, 15th Int'l. Symp. Control Rel. Bioact. Material, Abstract No. 89, 1998, pp. 147–148.

W. L. Chiou et al., *Preparation and Dissolution Characteristics of Several Fast–Release Solid Dispersions of Griseofulvin*, J. Pharm. Sci., vol. 58, No. 12, 1969, pp. 1505–1510.

W. L. Chiou et al., *Pharmaceutical Applications of Solid Dispersion Systems*, vol. 60, No. 9, 1971, pp. 1281–1301.

(List continued on next page.)

Primary Examiner—Thurman K. Page
Assistant Examiner—Blessing Fubara
(74) Attorney, Agent, or Firm—Burns, Doane, Swecker & Mathis, L.L.P.

(57) ABSTRACT

The invention relates to a novel biologically active composition which comprises a biologically active agent composition which comprises a biologically active agent to be released therefrom, said biologically active agent being dissolved and/or dispersed in a supersaturated state within a carrier, which carrier comprises a liquid and/or solid non-crystalline ester and/or polyester matrix, and where the precipitation of said biologically active agent is substantially, or completely, inhibited therein. Said supersaturated states is obtainable by subjecting one or more carrier staring substances(s) to such chemical reaction(s) that an ester and/or polyester matrix is provided, the biologically active agent being added after said chemical reaction(s) has (have) been completed.

39 Claims, 1 Drawing Sheet

OTHER PUBLICATIONS

Figure 1:
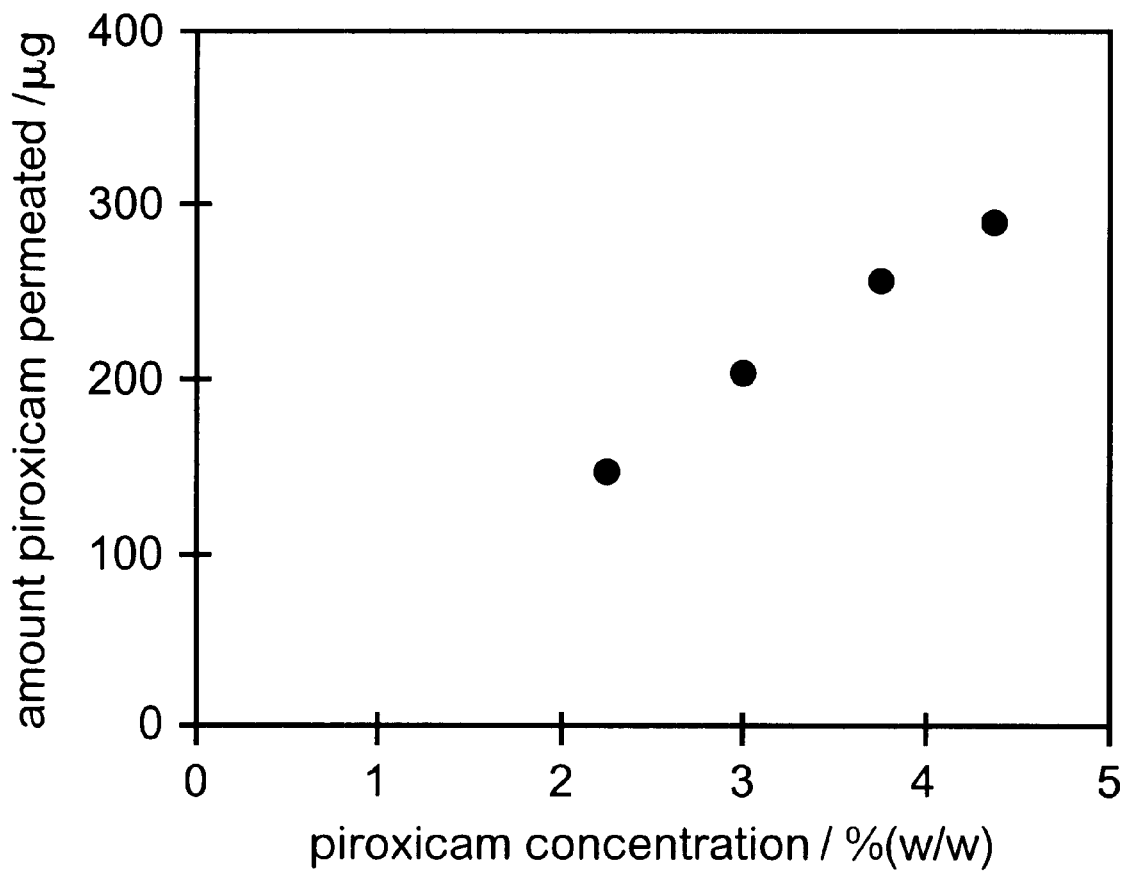

Rainier Lichtenberger et al., *Polymer Films From Aqueous Latex Dispersions As Carriers for Enhanced Transdermal Delivery of Lipophilic Drugs—Influence of Drug–Polymer Interactions and Formulation Parameters on Release Characteristics*, Conf. Proceedings, IBC Tech. Svcs. Ltd., London, 1989, pp. 360–366.

H. P. Merkle, *Transdermal Drug Delivery Systems*, Meth. and Find. Exp. Clin. Pharama. 11 (3), 1989, pp. 150–151.

D. Pramanick et al., *Copolyester of Citric Acid and 1,2, 6–Hexane Triol as a Matrix for Controlled Drug Release*, J. Polymer Materials (13), 1996, pp. 173–178.

\* cited by examiner

BIOLOGICALLY ACTIVE COMPOSITION

This application is a 371 of PCT/SE99/00823 filed May 12, 1989.

TECHNICAL FIELD

The present invention relates to a biologically active composition from which one or more biologically active components are to be released. More specifically, the invention relates to a biologically active composition wherein the biologically active agent is present in a supersaturated state within a carrier without being precipitated therefrom.

BACKGROUND OF THE INVENTION

From inter alia toxicological points of view, it is often preferred, upon treatment of diseases or symptoms thereof, to deliver drugs directly to their site(s) of action. It is well known that the risks of obtaining detrimental effects of systemic origin are often markedly reduced if a drug is delivered directly to its site(s) of action. Furthermore, systemic delivery often involves metabolism of the drug prior to its appearance at the site of action, which leads to a subsequent reduction of its biological effect. Another important aspect is that in e.g. cases of imminent overdosage, allergic reactions or administration of contraindicating drugs, it is easy to remove topical compositions in contrast to drugs administered per-orally or by injection.

As used herein, topical administration comprises inter alia dermal, sub-lingual, gingival, buccal, transdermal, nasal, vaginal and rectal administration, whereby the resulting biological effect may be local and/or systemic.

In e.g. dermal, nasal, vaginal, buccal or sub-lingual administration, only a very limited number of drugs are capable of permeating into the human body by themselves at a useful rate. Consequently, a lot of research has been conducted in order to investigate the possibility of both improving traditional non-invasive delivery techniques and developing novel non-invasive drug delivery systems or devices intended for systemic and/or internal use. Three fundamentally different approaches towards this objective have been disclosed.

Firstly, there is the well known possibility of improving the penetration properties of the drug by chemical modification thereof. After the drug has entered the body, its pharmacologically active form is obtained by chemical reaction(s) in vivo. However, this so called pro-drug approach is only occasionally a succesful alternative. There are several reasons therefor, such as i) the penetration rate of the pro-drug may still be too low, ii) the pro-drug may be toxic or otherwise harmful, or iii) the in vivo conversion to the active form of the drug is too slow and/or partially results in inactive or toxic compounds. A distantly related approach is the preparation of an ion pair between a drug and an appropriate counter ion. However, generally such an ion pair does not display any markedly improved penetration rate through human barriers.

Secondly, the properties of the barrier may be changed in order to facilitate the drug delivery. Methods of achieving this are e.g. ultra-sonication, applying of electrical current or the use of so called penetration enhancers in the composition. All of these methods act by disrupting the structure of the barrier, thereby facilitating drug diffusion through the barrier into the body, and/or improving the drug solubility in the barrier. However, the methods involving e.g. heat, ultra-sonication and electrical current are generally not designed for being easily managed by the patient in a convenient manner, and therefore require hospitalisation, which is a major disadvantage with said methods. In addition, all methods which are based on the approach of changing the barrier properties are questionable from a toxicological point of view due to the observations that i) adverse effects on the cells of the barrier have been demonstrated, and ii) a reduction of the protective properties of the barrier also result in increased penetration rate for any substance, not only the drug, that is present at the site of administration. It should also be mentioned, that a majority of the known chemical penetration enhancers require some time for the onset of their action, i.e. display a lag time of action, since they must be established in the barrier before the actual increase in penetration rate is observed.

Thirdly, the driving force of the drug for entering the body can be changed. That is, the difference in the electrochemical potential of the drug between the drug reservoir and the body can be increased. Drug delivery systems based on this approach result in a high flux of the drug through the barrier and usually also display a reduced lag time of action.

In methods based on iontophoresis, this approach is utilised by applying an electrical potential gradient across the barrier obviously, these methods are mainly suitable for drugs having a net charge and are therefore much less efficient for uncharged and zwitterionic species, since the flux of the two latter species is improved mainly due to e.g. osmotic and electroosmotic driving forces. Iontophoresis methods also have the disadvantage that they may alter the structure of the barrier.

In another approach, the flux of a drug into the body can be enhanced by increasing the chemical potential of the drug in the carrier therefor. This is normally performed by chemical optimisation of the drug composition by adjusting the degree of saturation of the drug in said carrier. The methods based on this approach offer several advantages as compared to the previously mentioned methods, since the flux of the drug is increased in comparison with subsaturated and saturated systems. Furthermore, the properties of the barrier itself are comparatively less affected and the lag time of initiation for the pharmacological effect is reduced. There are two particularly important aspects in this approach:

i) creation of an initial high chemical potential of the drug in the composition ii) maintenance of a high chemical potential of the drug in the vicinity of the barrier after the application of the composition.

Therefore, it is usually desirable to prepare pharmaceutical compositions which are saturated with respect of the drug. During application, another important aspect of said composition is that the solubility and diffusion properties of the drug in the used vechicle must preclude depletion of the drug in the vicinity of the barrier. Examples of compositions used for this purpose are microemulsions and emulsions.

Another approach towards keeping the composition saturated is the use of an excess amount of drug (non-solubilised) in the carrier, whereby the drug is subsequently dissolved as it replaces the drug which has penetrated through the barrier.

Yet another approach is the use of a supersaturated composition of the drug. Here, the driving force of the drug to penetrate the barrier is higher than in the saturated composition, since the drug in a supersaturated composition has higher chemical potential in comparison with the corresponding saturated composition. For example, such compositions have been prepared according to the following means or principles: i) dissolving the drug at temperatures and/or pressures at which the solubility of the drug is higher as compared to those temperatures and/or pressures that are relevant for medication (W. L. Chou and S. Riegelmann, *J. Pharm. Sci.*, Vol.60, No.9, pp.1281–1302, 1971; WO 97/10812), ii) using solid dispersions or eutectic mixtures or solid drug particles of low degree of crystallinity or of high energy polymorphs (W. L. Chou and S. Riegelmann, supra), iii) mixing a saturated drug solution with a non-solvent therefor, thereby performing a merely physical operation, in situ or prior to application, with or without the presence of an antinucleating agent (U.S. Pat. No. 4,940,701; U.S. Pat. No. 4,767,751), iv) solvent evaporation to the surrounding air (Coldman et al., *J. Pharm. Sci.*, 58, No.9 (1969), pp 1098–1102), v) solvent penetration into the human body, vi) water uptake into the composition from the human body, vii) pH-changes in the composition caused by $H^+$-uptake from the human body, or viii) dispersing an aqueous solution or emulsion of a drug in an aqueous dispersion of a polymer latex (Lichtenberger et al., "Polymer films from aqueous polymer dispersions as carriers for transdermal delivery of lipophilic drugs", 15th Int Symp CRS:Basel 1988; Abstr 89). An important common denominator of iv)-vii) is that the supersaturation is not initally present in the composition, and is therefore de facto not accomplished until the composition is applied to a human body. Furthermore, a major problem with all the compositions i)-viii) is that the drug generally precipitates in a relatively short time, in which case the saturation degree becomes markedly reduced.

DD 217 989 discloses a supersaturated composition, wherein the carrier matrix is an acrylate (scopacryl d), optionally in combination with an excipient, which matrix is claimed to prevent recrystallisation of a supersaturated drug present therein:

W. L. Chou and S. Riegelmann (*J. Pharm. Sci.*, Vol.58, No. 12, pp.1505–1510, 1969) have reported that in matrices of higher molecular weight polyethylene glycols, precipitation of a supersaturated drug dissolved therein is usually sluggish.

Other prior art of interest is WO 97/10812, which discloses a method for preparing supersaturated systems by controlled melting of an admixture of a drug and a polymeric carrier material.

Mention can also be made of GB 2 306 885, which discloses a composition, where a supersaturated state is attained in an aqueous carrier matrix.

As prior art, reference is also made to WO 97/00670, which discloses a composition based on ingredients similar to those utilized in the present invention. However, said reference does not disclose or suggest any supersaturated state or even less those features of the present invention which have been found crucial to impart a stable, supersaturated state to such a composition.

In summary, none of the above prior art discloses or suggests the essential features of the supersaturated composition according to the present invention.

GENERAL DISCLOSURE OF THE INVENTION

The inventors have now found a novel approach for obtaining a biologically active composition which provides both unexpected stability and high delivery rate to a supersaturated active component present therein. According to the disclosed invention, a biologically active agent is present in a substantially stable supersaturated state within a carrier therefor.

Briefly, it has been found that by subjecting carrier starting substance(s) to such chemical reaction(s) that a carrier matrix of substantially non-crystalline, or amorphous, nature is created, the carrier matrix thus obtained has the property to inter alia maintain a biologically active agent in a surprisingly stable supersaturated state. In a biologically active composition thus prepared, the precipitation of said agent is substantially, or completely, inhibited by said carrier matrix per se.

The term "biologically active agent", as used herein, also comprises such progenitors thereto which are readily transformable, e.g. enzymatically and/or hydrolytically, to a biologically active agent per se.

Thus, the present invention relates to a novel biologically active composition which comprises a biologically active agent to be released therefrom, said biologically active agent being dissolved and/or dispersed in a supersaturated state within a carrier, which carrier is a liquid and/or solid substantially non-crystalline matrix, and where the precipitation of said biologically active agent is substantially, or completely, inhibited therein.

The term "liquid" as used in connection with the present invention should be interpreted in a broad sense, viz as any material being a mobile or viscous liquid, rubber, glass or plastic; thus including solutions, creams, pastes, ointments and gels within the scope of the claims.

The present invention also relates to a method for the preparation of a biologically active composition comprising a biologically active agent dissolved and/or dispersed in a supersaturated state in a carrier therefor as well as to said composition for use as a medicament.

The term "pharmaceutically active agent", as used herein, also comprises such progenitors, e.g. pro-drugs, which are readily transformable, e.g. enzymatically and/or hydrolytically, to a pharmaceutically active agent per se.

One of the objects of the present invention is thus to provide a supersaturated composition which does not display any significant precipitation or loss of effect during long-term storage at room temperature, or even at above or below room temperature, during e.g. months or even years.

Another object of the present invention is to provide a supersaturated composition which does not display any significant precipitation or loss of effect during its application to a human or animal patient.

Still another object of the present invention is to provide a carrier matrix which is suitable in preparation of a composition having a particularly high degree of supersaturation of a drug (vide infra).

A further object of the present invention is to provide a carrier matrix which is particularly suitable for attaining supersaturation of biologically active agents which are sensitive towards hydrolysis in carrier matrices based on water or otherwise are chemically and/or physically unstable.

Yet another object of the present invention is to provide a stable supersaturated composition which is easily handled and does not require professional assistance upon use thereof.

As a result of the high delivery rate of its active component (s), yet another object of the present invention is to provide a composition which allows for efficient topical treatment, preferably dermal or transdermal administration to small areas, which is a general advantage in the topical administration of drugs.

DETAILED DISCLOSURE OF THE INVENTION

More specifically, the invention refers to a biologically active composition comprising a biologically active agent dissolved and/or dispersed in a carrier therefor, wherein said carrier comprises, or is, a liquid and/or solid substantially non-crystalline ester and/or polyester matrix in which said biologically active agent is present in a supersaturated state and, the precipitation of said biologically active agent being substantially, or completely, inhibited by said matrix.

Said supersaturated state is obtainable by subjecting one or more carrier starting substance(s) to such chemical reaction(s) that a non-crystalline ester and/or polyester carrier matrix is provided, a biologically active agent being added after said chemical reaction(s) has (have) been completed.

Other preferable embodiments of the composition claimed will be defined in the claims and referred to below in connection with the method.

Thus, the present invention also discloses a method for the preparation of a biologically active composition comprising a biologically active agent dissolved and/or dispersed in a carrier therefor, wherein a carrier starting substance, or a mixture of two or more different starting substances, is (are) subjected to such chemical reaction(s) that a liquid and/or solid non-crystalline ester and/or polyester carrier matrix is formed, the biologically active agent being added to said carrier matrix after said chemical reaction(s) has (have) been completed and in such an amount that a supersaturated state is obtained. Generally this means that the ester or polyester forming reaction(s) is (are) performed in the absence of said biologically active agent, after which said agent is added to said formed non-crystalline matrix; the addition of said biologically active agent being made using an amount such that a supersaturated state is obtained.

In a preferred embodiment of the invention, said biologically active agent is being added in solid and/or liquid, i.e. melted, state and is subsequently dissolved in said non-crystalline matrix, preferably above room temperature.

In another embodiment of the invention, said biologically active agent is being added as a solution or dispersion, which is subsequently dissolved in said non-crystalline matrix, preferably above room temperature. In yet another embodiment of the invention, said biologically active agent is added in the form of a high energy polymorph thereof, which is subsequently dissolved in said non-crystalline matrix.

According to the present invention, above room temperature is a temperature above about 25° C., such as about 25–200° C., preferably about 30–150° C. Examples of other suitable temperatures are about 35–100° C. and 40–80° C.

The particular addition method used for said agent can be any common inclusion technique available to a person skilled in the art, and said solution or dispersion of the biologically active agent can be prepared inter alia by solvent evaporation, freeze-drying or by use of any one of the methods i)-vil) (vide supra).

Preferably, in the composition according to the invention as well as in the method for preparation thereof, the formed non-crystalline ester and/or polyester matrix is used as solvent or dispersing medium.

Said chemical reaction(s) generally comprise one or more esterifying reactions.

Said carrier starting substance(s), which are subsequently subjected to said chemical reaction(s) above, are selected from monomers, such as diacids, triacids and higher acids, alcohols, including diols, triols and higher alcohols, saccharides and derivatives thereof, acrylate saccharides, including acrylate starch, and oligomers, polymers or prepolymers thereof.

It is to be understood by a person skilled in the art, that said chemical reaction(s) is performed to such a degree of completion that a desired non-crystalline ester and/or polyester carrier matrix is obtained, which matrix is optimal for a particular biologically active agent in a particular context. As a non-limiting example, said non-crystalline ester and/or polyester carrier matrix may contain a minor amount of starting substance(s), and still being within the scope of the present invention.

In a preferred embodiment of the present invention, the carrier starting substances are an acid and an alcohol, preferably citric acid and propylene glycol, said non-crystalline matrix comprising an ester and/or polyester thereof.

In an alternative embodiment, the starting substance is one bi- or multi-functional substance only, which when subjected to said chemical reaction(s) provides the desired non-crystalline carrier matrix by chemical reaction(s) with itself. In a non-limiting disclosure, such a starting substance can be citric acid, which when subjected to esterifying conditions provides a non-crystalline citric acid ester and/or polyester matrix according to the invention.

In another embodiment of the invention, an ester and/or polyester are (is) subjected to such chemical reaction(s), e.g. hydrolysis, that a non-crystalline ester and/or polyester carrier matrix is provided, after which a biologically active agent is added in an amount such that a supersaturated composition is obtained.

According to the present invention, suitable chemical reaction(s) involve(s) subjecting said carrier starting substance(s) to such esterifying conditions which are normally used, according to standard reference literature, for the selected starting substance(s) or combinations thereof. Furthermore, such esterifying conditions should be chosen in order to optimise the manufacturing procedure, in respect of e.g. manufacturing time and attainable degree of supersaturation, for the particular biologically active agent used. Typically, said conditions comprise e.g. subjecting said carrier starting substance(s) to a temperature from around −50° C. to around 300° C., preferably around 0–150° C. Other examples of useful temperature ranges are 20–100° C. and 50–80° C. Said temperature ranges are particularly preferred when the starting substance(s) are a mixture of citric acid and propylene glycol. Naturally, said chemical reaction(s) are selected and performed so that in each case the maximum or optimum delivery rate of said biologically active agent is obtained.

Preferably, said chemical reaction(s) is (are) performed for a time period of from 1 minute to 6 months, preferably from 0,5 hours to 4 months. As an example, said time period may also be from 1 hour to 3 months or from 1 to 2 months.

According to the present invention, monofunctional monomers can be introduced into said chemical reaction(s) as a means of controlling the end point of the reaction(s).

It deserves to be mentioned, that regulation of the molecular weight, and distribution thereof, of the molecules which constitute the formed non-crystalline matrix allows for controlling the solubility of the biologically active agent agent in said matrix. The molecular weight distribution is probably also of importance for the diffusion rate of said agent through said matrix.

Preferably, the biologically active composition according to the invention consists of one liquid or solid phase only.

Non-limiting examples of biologically active agents, preferably pharmaceutically active agents, which are suitable for use in the present invention are e.g., guanosides, corticosteroids, psychopharmaceutical hormones, oxicams, peptides, proteins as well as agents selected from the group of antibiotics, antivirals, antimicrobials, anticancer agents, antifungals, oestrogens, antiinflammatory agents, neuroleptic agents, melanocyte stimulants and gland stimulants, preferably stimulators of sebaceous and pilo-sebaceous glands, and agents with an effect on mast cell secretion.

In the most preferred embodiment of the present invention the carrier starting substance(s) are subjected to an esterifying reaction without the presence of said biologically active agent. To the non-crystalline ester and/or polyester matrix thus obtained, a biologically active agent is added in solid state and is subsequently dissolved above room temperature. When the composition thus prepared is allowed to attain room temperature, a stable supersaturated composition is thereby prepared.

For some biologically active agents it is preferred to prepare a supersaturated composition shortly before administration thereof. Indeed, the present composition is useful for such preparations in addition to it being suitable for supersaturated compositions intended for long-term storage and application. As for the choice of a suitable degree of supersaturation of the biologically active agent in the present composition, it is known from the laws of thermodynamics that within a given period of time the danger of precipitation increases with the degree of supersaturation. Still, the present composition is also suitable in such particular preparations where a very high degree of supersaturation is desirable, despite a somewhat increased danger of precipitation.

The scope of the present invention is not limited to the specific embodiments disclosed above, and the disclosed invention may optionally be combined with the methods i)-vii) (vide supra) in any suitable manner, if deemed necessary in any particular case. As a non-limiting example, the pH of the composition prepared according to the invention may optionally be subsequently modified by inclusion of a suitable acidic or basic compound, if useful in a particular context.

The following non-limiting example will illustrate the present invention further.

Experimental Part

Reference composition:

An excess of piroxicam was added to PEG400, and the mixture was stirred for 2 weeks at room temperature. After sedimentation and centrifugation, HPLC analysis showed that a resulting solubility of s=1.6% was obtained. Four supersaturated solutions of piroxicam in PEG400 were then manufactured, each one having a degree of saturation (DS=concentration/solubility) of 1.4, 1.8, 2.3 and 2.7, respectively. They were prepared by heating the corresponding amount of piroxicam in PEG400 to 80° C. for 30 min under stirring, followed by equilibration to room temperature, thereby yielding supersaturated solutions. The time for precipitation of piroxicam to occur ($t_p$) upon storage at room temperature was monitored by visual inspection, and the results are shown in Table 1.

TABLE 1

Time for precipitation of piroxicam from a supersaturated solution thereof in PEG400.

| Solution | piroxicam conc. % (w/w) | DS* | $t_p$ |
|---|---|---|---|
| 1 | 2.2 | 1.4 | 5 h < $t_p$ < 21 h |
| 2 | 3.0 | 1.8 | $t_p$ < 0.5 h |
| 3 | 3.7 | 2.3 | $t_p$ < 0.5 h |
| 4 | 4.4 | 2.7 | $t_p$ < 0.5 h |

*DS = 1 equals 1.6% (w/w) piroxicam in PEG400 (vide supra)

Composition according to the invention:

A composition was manufactured by mixing 6 parts of citric acid and 4 parts of propylene glycol (starting substances) at room temperature in a glass container which was subsequently sealed. The temperature was raised to and maintained at 80° C. under stirring for 2 h. The mixture was then allowed to attain room temperature, followed by subjecting it to 70° C. for 26 days, freezer temperature for 235 days and finally room temperature for 1 day. The resulting mixture was a clear, viscous and almost colourless solution. The above outlined procedure results in the formation of ester bonds between the citric acid and propylene glycol, whereby an ester carrier matrix is formed. According to HPLC analysis, said solution (i.e. carrier matrix) had a content of unreacted citric acid of only 4.5%.

Said solution was then split into 4 separate solutions, each to which an appropriate amount of piroxicam (see Table 2) was added, followed by heating to 97° C. for at least 30 min or until all piroxicam had been dissolved. After attaining room temperature, the supersaturated compositions X1–X4 were thereby obtained, and their $t_p$-values were investigated.

TABLE 2

$T_p$ value for supersaturated piroxicam in the compositions X1–X4 (w = weeks)

| Composition | piroxicam conc. % (w/w) | DS* | $t_p$ |
|---|---|---|---|
| X1 | 2.2 | 1.8 | $t_p$ > 3 w |
| X2 | 3.0 | 2.5 | $t_p$ > 3 w |
| X3 | 3.8 | 3.2 | $t_p$ > 3 w |
| X4 | 4.4 | 3.6 | 2 w < $t_p$ < 3 w |

*The permeation rate at saturation was assumed to be 82 µg per 24 h.

The DS values shown in Table 2 were obtained by use of Franz diffusion cell measurements, and to a person skilled in the art, it is well known that the permeation rate of a compound through a Silastic membrane in a Franz diffusion cell experiment is a direct measure of the thermodynamic potential of said compound. Moreover, a direct correlation between the thermodynamic potential and the degree of saturation (DS) can often be assumed. Therefore, the equation DS=permeation rate/permeation rate at saturation was assumed to be valid when estimating the DS values.

As can be seen in Table 2, the $t_p$ value for all the compositions X1–X4 exceeds 2 weeks. At the time of filing the present application, no precipitation had yet been observed in the compositions X1–X3. Indeed, the experiments depicted in Table 2 substantiate the precipitation preventing properties of the carrier matrix according to the present invention, particularly in comparison with the experiments depicted in Table 1 above.

Further more the increasingly higher degree of supersaturation of piroxicam in the compositions X1–X4 results in an increased permeation rate, i.e. an increasingly higher thermodynamic potential. This was evidenced by investigating the permeation rate of peroxicam through a membrane (Silastic sheeting NRV, 0.005 inches, serial #SM097307) by using a Franz diffusion cell (FDC-400 Crown Glass Company) with a cell opening area of 2.001 cm². The permeation rate measurements were performed for 24 h at 25° C. and a 7:3 (w/w) PEG400/$H_2O$-mixture was used as acceptor phase on the opposing side of the membrane. The donor and acceptor phase were both sealed with parafilm, and each experiment was performed in triplicate. As a reference, the permeation rate from a satruated propylene glycol solution of piroxicam was determined to be 82 µg per 24 h in a Franz diffusion cell experiment. The results are shown in FIG. 1.

In summary, it is clearly realised that biologically active compositions which are prepared or obtainable in accordance with the present invention are useful as medicaments. Furthermore, the biologically active compositions according to the invention are also useful in a medicinal context, such as in cosmetic skin products. More specifically, said compositions should be highly effficient in dermal application to a mammal, preferably man, as well as in any general application where a biological barrier is to be penetrated by a biologically active agent.

What is claimed is:

1. A biologically active composition comprising a biologically active agent to be released therefrom, said biologically active agent being dissolved or dispersed in a carrier therefor, wherein said carrier comprises a liquid non-crystalline ester or polyester matrix in which said biologically active agent is present in a supersaturated state.

2. A composition according to claim 1, wherein said supersaturated state is obtainable by subjecting one or more carrier starting substance(s) to a chemical reactions(s) such that a non-crystalline liquid ester or polyester matrix is formed, the biologically active agent being added to said liquid matrix after said chemical reaction(s) has been completed.

3. The composition according to claim 2, wherein said non-crystalline ester or polyester matrix is a solvent or dispersing medium for said biologically active agent.

4. The composition according to claim 2, wherein said biologically active agent is a solid or liquid which is subsequently dissolved in said matrix.

5. The composition according to claim 2, wherein said biologically active agent is a solution or dispersion which is subsequently dissolved.

6. A composition according to claim 2, wherein said biologically active agent is added in the form of a high energy polymorph thereof or as a solid with low degree of crystallinity.

7. The composition according to claim 2, wherein said biologically active agent is an agent which is added or dissolved at a temperature around 25–200° C.

8. A composition according to claim 2, wherein said chemical reaction(s) comprise one or more esterifying reactions.

9. The composition according to claim 8, wherein the esterifying reaction(s) is selected and performed so as to provide optimal delivery rate of said biologically active agent.

10. The composition according to claim 2, wherein said chemical reaction(s) involve(s) subjecting said carrier starting substance(s) to a temperature of from around −50° C. to around 300° C.

11. The composition according to claim 2, wherein said chemical reaction(s) is conducted for a time period of from 1 minute to 6 months.

12. A composition according to claim 2, wherein said carrier starting substance, or mixture of two or more different carrier starting substances, is selected from the group consisting of acids, alcohols, saccharides, acrylate saccharides, oligomers, polymers and prepolymers thereof.

13. A composition according to claim 12, wherein the acid is a monomeric acid and the alcohol is a monomeric alcohol.

14. A composition according to claim 13, wherein aid monomeric acid is citric acid.

15. A composition according to claim 13, wherein said monomeric alcohol is propylene glycol.

16. A composition according to claim 1, which consists of one liquid phase only.

17. A composition according to claim 1, wherein the biologically active agent is a pharmaceutically active agent.

18. A composition according to claim 17, wherein the pharmaceutically active agent is selected from the group consisting of guanosides, corticosteroids, psychopharmaceutical hormones, oxicams, peptides, proteins, antibiotics, antivirals, antimicrobials, anticancer agents, antifungals, oestrogens, antiinflammatory agents, neuroleptic agents, melanocyte stimulants and gland stimulants, and agents with an effect on mast cell secretion.

19. A composition according to claim 17, wherein the composition is administered as a medicament.

20. A composition according to claim 1 for topical application to a mammal.

21. A method for the preparation of a biologically active composition comprising a biologically active agent dissolved or dispersed in a non-crystalline ester or polyester carrier therefor, wherein a carrier starting substance, or a mixture of two or more different carrier starting substances, is subjected to a chemical reaction(s) such that a liquid non-crystalline ester or polyester carrier matrix is formed, the biologically active agent being added to said liquid carrier matrix after said chemical reaction(s) have been completed and in such an amount that a supersaturated state is obtained.

22. A composition according to claim 3 wherein said biologically active agent is a solid or liquid which is subsequently dissolved in said matrix.

23. A composition according to claim 3, wherein said biologically active agent is as a solution or dispersion which is subsequently dissolved.

24. A composition according to claim 3, wherein said biologically active agent is a solid with no crystallinity.

25. A composition according to claim 14, wherein said monomeric alcohol is propylene glycol.

26. A composition according to claim 18, wherein the composition is administered as a medicament.

27. The composition of claim 4, wherein the biologically active agent is an agent which is dissolved in said matrix at a temperature above room temperature.

28. The composition of claim 5, wherein the biologically active agent is an agent which is dissolved in said matrix at a temperature above room temperature.

29. The composition of claim 2, wherein the biologically active agent is an agent which is dissolved at a temperature of around 30–150° C.

30. The composition of claim 2, wherein the carrier starting substances are carrier starting substances subjected to a temperature of around 0–150° C.

31. The composition of claim 2, wherein the chemical reactions are conducted for a time period of from 0.5 hours to 4 months.

32. The composition of claim 12, wherein the acids are selected from the group consisting of diacids, triacids and higher acids.

33. The composition of claim 12, wherein the alcohols are selected from the group consisting of diols, triols and higher alcohols.

34. The composition of claim 12, wherein the acrylate saccharide is acrylate starch.

35. The composition of claim 18, wherein the gland stimulants are stimulators of sebaceous and pilo-sebaceous glands.

36. The composition of claim 20, wherein the topical application is dermal application.

37. The composition of claim 20, wherein the mammal is a human.

38. The composition of claim 22, wherein the biologically active agent is dissolved in said matrix at a temperature above room temperature.

39. The composition of claim 23, wherein the biologically active agent is dissolved in said matrix at a temperature above room temperature.

* * * * *